United States Patent [19]

Cullinan et al.

[11] Patent Number: 4,845,200

[45] Date of Patent: Jul. 4, 1989

[54] IMMUNOGLOBULIN CONJUGATES

[75] Inventors: George J. Cullinan, Trafalgar, Ind.; George F. Rowland, Gerrards Cross; Robin G. Simmonds, Wokingham, both of England

[73] Assignee: Lilly Industries Limited, London, England

[21] Appl. No.: 877,598

[22] Filed: Jun. 23, 1986

Related U.S. Application Data

[63] Continuation of Ser. No. 593,443, Mar. 26, 1984, abandoned.

[30] Foreign Application Priority Data

Mar. 30, 1983 [GB] United Kingdom ............... 8308857

[51] Int. Cl.$^4$ ..................... A61K 39/395; C07K 3/08
[52] U.S. Cl. .................................. 530/391; 530/387; 530/389; 530/402; 530/405; 530/406; 530/828; 424/85.91
[58] Field of Search .................... 530/387, 389, 391; 424/85

[56] References Cited

U.S. PATENT DOCUMENTS 4,507,234 3/1985 Kato et al. ..................... 530/389

OTHER PUBLICATIONS

Vitella et al, Science, 219, 644–650, Feb. 1983.
Rowland et al, Cancer Immunol. Immunother, 19: 1–7, (1985).

Primary Examiner—Margaret Moskowitz
Assistant Examiner—Jeff P. Kushan
Attorney, Agent, or Firm—Robert A. Conrad; Leroy Whitaker

[57] ABSTRACT

A conjugate comprising a vinca moiety convalently linked at the 4-position via a group of the formula —OCOXCO— where X represents a single chemical bond or an optionally substituted $C_{1-10}$ chain, to an immunoglobulin or an immunoglobulin fragment.

The conjugates are useful in the treatment of cancer.

17 Claims, No Drawings

IMMUNOGLOBULIN CONJUGATES

This application is a continuation of application Ser. No. 593,443, filed Mar. 26, 1984, now abandoned.

This invention relates to novel immunoglobulin conjugates with pharmaceutical properties and, in particular, cytostatic activity.

A group of compounds which are cytostatic and widely employed in the treatment of cancer are the vinca (indole-dihydroindole) alkaloids and drugs derived from them. The chemotherapeutic use of these drugs is sometimes limited in its effectiveness by unwanted side effects on the patient and efforts to minimise such effects have been the subject of much research. For example, British Pat. No. 2 090 837 describes a conjugate of vindesine, one of the vinca alkaloid drugs referred to above, with an immunoglobulin, in which the vindesine moiety is linked directly at the 3-position of the vindesine molecule. When the immunoglobulin is an antibody the conjugate concentrates at the site of action with a reduction in toxic effect on other tissues and a potential reduction of undesirable side-effects in the patient.

The invention provides a novel conjugate comprising a vinca moiety covalently linked at the 4-position via a group of the formula —OCOXCO— where X represents a single chemical bond or an optionally substituted $C_{1-10}$ chain, to an immunoglobulin or an immunoglobulin fragment. The novel conjugate is a derivative of a vinca, such as for example, a 4-acetoxy or 4-hydroxy antineoplastic dimeric indole-dihydroindole alkaloid and can have one or more such vincal moieties covalently attached to it.

The immunoglobulin or fragment is an antibody or a fragment of an antibody with antigen recognising properties. The preferred immunoglobulin material is an antibody or a fragment of an antibody adapted for recognition of antigens on the surface of unwanted cells of the type occurring in the human body. However immunoglobulin materials of other kinds are also included within the scope of the invention since they may be of use in treatment of animals and in control and assay experiments.

The novel conjugates are useful, inter alia, in the treatment of cancers. They are potentially more effective and have fewer side effects by virtue, of their ability to increase the concentration of the cytotoxic drug at the site of action. The linkage of the drug moiety via the "spacer" group —OCOXCO— frequently enables a greater drug concentration on the immunoglobulin to be produced, and can thus increase the efficacy of the conjugate. The invention also includes conjugates for use in an indirect system in which they are employed to recognise an antibody specific to the cell surface antigen.

More particularly, the conjugates of the invention can be represented by the following formula

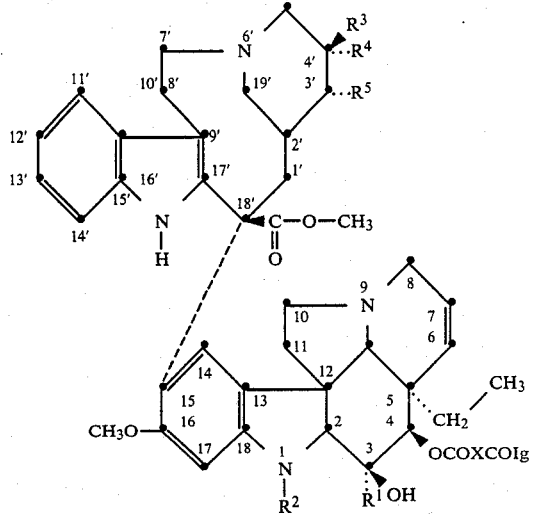

(I)

in which Ig represents an immunoglobulin or an immunoglobulin fragment and X is as defined above; and in which $R^1$ is COOH, $COOC_{1-3}alkyl$ or CO—$R^6$, where $R^6$ is $NH_2$, NH—$C_{1-3}alkyl$, NH—$CH_2CH_2Cl$, 1-pyrrolidyl, 1-piperidinyl or NH—$CH_2CH_2YCH_3$ where Y is S or O; $R^2$ is H, $CH_3$ or CHO; and when $R^4$ and $R^5$ are taken singly, $R^5$ is H, and one of $R^3$ and $R^4$ is ethyl and the other is H or OH; and when $R^4$ and $R^5$ are taken together with the carbons to which they are attached, they form an oxirane ring, and $R^3$ is ethyl. The immunoglobulin, or fragment, can be modified by one or more of the vinca residues shown.

Some of the well known vinca alkaloids from which the above conjugates are derived have, for example, the vinca moiety of formula (I) above in which the 4-position is variously substituted as, for example, vinblastine in which $R^1$ is $COOCH_3$, $R^2$ is methyl, $R^3$ is hydroxyl, $R^4$ is ethyl, $R^5$ is hydrogen and the substituent at the 4-position is acetoxy; vindesine in which $R^1$ is $CONH_2$, $R^2$ is methyl, $R^3$ is hydroxyl, $R^4$ is ethyl, $R^5$ is hydrogen and the substituent at the 4-position is —OH; vincristine in which $R^1$ is $COOCH_3$, $R^2$ is formyl, $R^3$ is hydroxyl, $R^4$ is ethyl, $R^5$ is hydrogen, and the substituent at the 4-position is acetoxy; leurosidine in which $R^1$ is $COOCH_3$, $R^2$ is methyl, $R^3$ is ethyl, $R^4$ is hydroxyl, $R^5$ is hydrogen and the substituent at the 4-position is acetoxy; VLB "A" (4'-deoxyvinblastine) in which $R^1$ is $COOCH_3$, $R^2$ is methyl, $R^3$ and $R^5$ are hydrogen, $R^4$ is ethyl and the substituent at the 4-position is acetoxy; VLB "B" (4'-deoxyleurosidine) in which $R^1$ is $COOCH_3$, $R^2$ is methyl, $R^3$ is ethyl, $R^4$ is hydrogen, $R^5$ is hydrogen and the substituent at the 4-position is acetoxy; leurosine in which $R^1$ is $COOCH_3$, $R^2$ is methyl, $R^3$ is ethyl, $R^4$ and $R^5$ taken together form an α-epoxide (oxirane) ring and the substituent at the 4-position is acetoxy; and leuroformine (N-formyleurosine) in which $R^1$ is $COOCH_3$, $R^2$ is formyl, $R^3$ is ethyl, $R^4$ and $R^5$ taken together form an α-epoxide ring and the substituent in the 4-position is acetoxy.

Literature references to the parent alkaloids of the 4-desacetyl derivatives are as follows: leurosine (U.S. Pat. No. 3,370,057), VLB (U.S. Pat. No. 3,097,137), leurosidine (vinrosidine) and leurocristine (vincristine) (both U.S. Pat. No. 3,205,220), desmethyl VLB (U.S. Pat. No. 3,354,163), vindesine and other 3-carboxamides (U.S. Pat. No. 4,203,898), vinblastinoic acid, vincristinoic acid, etc. (U.S. Pat. No. 4,012,390), 4'-epivincristine (U.S. Pat. No. 4,143,041) leuroformine, formylleurosine (U.S. Pat. No. 4,279,816), and deoxy VLB "A" and "B" [*Tetrahedron Letters,* 783 (1958)]. Other vinca alkaloids are disclosed in U.S. Pat. Nos. 4,166,810 and RE 30,560.

The group X represents a bond or an optionally substituted $C_{1-10}$ chain and is ultimately derived from the corresponding dicarboxylic acid HOOCXCOOH. The group is preferably $C_{1-4}$ straight chain alkylene, $C_{2-8}$-branched alkylene, $C_{2-4}$alkenylene, $C_{3-4}$alkynylene, $C_{3-6}$cycloalkylene, phenylene, hydroxy-substituted $C_{1-4}$alkylene or a direct bond.

Groups illustrative of X include methylene, ethylene, propylene, butylene, vinyl, propenylene, butenylene, butynylene, ethynylene, hydroxyethylene, 1,2-dihydroxyethylene, 1,2-dimethyl ethylene, 1,2,3,4-tetrahydroxybutylene, 3,4-dimethylbutylene, 1,4-cyclohexylene, 1,4-phenylene, 1,2-phenylene and the like. Preferably X is $C_{1-4}$alkylene, $C_{2-4}$alkenylene, $C_{2-4}$alkynylene, $C_{3-6}$cycloalkylene or phenylene and is especially $C_{1-4}$alkylene.

Immunoglobulins specific to antigens on the surface of cells to be killed, and techniques for their production from the serum of immunised animals or by culturing hybridomas secreting monoclonal products, are well known. The preferred type of antibody for use in the invention is an immunoglobulin of the IgG class. Some representative immunoglobulins are as follows, mono- or polyclonal antibodies to (i) human or animal tumour associated antigens
(ii) human B- and T-cell antigens
(iii) human Ia antigens
(iv) viral, fungal and bacterial antigens
(v) cells involved in human inflammatory or allergic reactions Of the preferred antibodies to human or animal tumour associated antigens there may be mentioned:
(i) Ig from goats or sheep immunised with carcinoembryonic antigen
(ii) Ig from rabbit antiacute lymphoblastic leukemia serum
(iii) Ig from various primate antisera raised against acute lymphoblastic leukemia, acut myleoblastic leukemia, chronic lymphoblastic leukemia and chronic granulocytic leukemia
(iv) Ig from goats or sheep immunised with lung carcinoma material
(v) monoclonal Ig from mouse hybridomas secreting anti-human colorectal carcinoma antibodies
(vi) monoclonal Ig from mouse hybridomas secreting anti-human melanoma antibodies
(vii) monoclonal Ig from mouse hybridomas secreting antibodies reacting with human leukemia cells
(viii) monoclonal Ig from mouse hybridomas secreting antibodies reacting with human neuroblastoma cells
(ix) monoclonal Ig from mouse hybridomas secreting antibodies reacting with human breast cancer antigens
(x) monoclonal Ig from mouse hybridomas secreting antibodies reacting with human ovarian carcinoma cells
(xi) monoclonal Ig from mouse hybridomas secreting antibodies reacting with human osteosarcoma cells
(xii) monoclonal Ig from mouse hybridomas secreting antibodies to lung carcinoma.

As indicated above, the conjugate can also be made with immunoglobulin fragments, referred to as Fab, Fab' (ab')₂ or IgM monomer derived from an antibody by, for example, proteolytic enzyme digestion. Such materials and methods of preparation are well known and it may be mentioned that preferred proteolytic enzymes are pepsin and papain.

Preferred conjugates of the invention are those of formula (I) above in which $R^1$ is COOMe or $CONH_2$, $R^2$ is methyl or formyl, $R^3$ is hydroxyl, $R^4$ is ethyl and $R^5$ is hydrogen, notably those derived from desacetylvinblastine and vindesine. Preferably the hydrophilic group X takes the value $C_{1-4}$alkylene and Ig is preferably a monoclonal antibody to human or animal tumour antigen.

The conjugates of the invention can be prepared by reacting an immunoglobulin or an immunoglobulin fragment with a hemi-acid derivative comprising a vinca moiety having a group of the formula —OCOXCOZ attached at the 4-position, where X represents a bond or an optionally substituted $C_{1-10}$chain and Z is a leaving group.

More particularly the process of the invention comprises reacting an immunoglobulin or immunoglobulin fragment with a compound of the formula

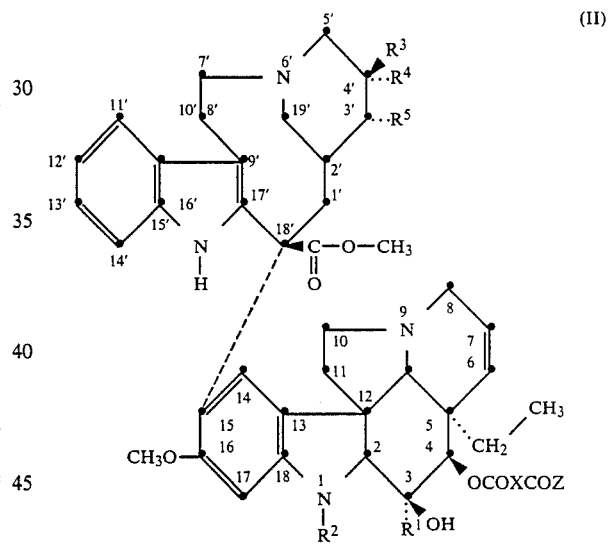

in which X, $R^1$, $R^2$, $R^3$, $R^4$ and $R^5$ have the values given for these radicals in formula (I) above and Z is a leaving group.

In the above formula (II) Z is a leaving group which can be any of the well known groups employed in peptide chemistry to establish a covalent amide link (—CONH—) between the conjugate and a free amino group on the immunoglobulin molecule or fragment. Such groups are well known in the art and are discussed for example, in Peptide Synthesis by M. Bodanszky, Y. S. Kalusner and M. A. Ondetti, Second Edition (1976) John Wiley & Sons, notably pages 85 to 136. It may be mentioned that Z can be an azide (—N₃) group, a halogen atom for example bromine and especially chlorine, an acyloxy group of the formula $R^7CO.O$ where $R^7$ is an aliphatic or aromatic residue such as for example $C_{1-3}$alkyl, an alkoxy preferably $C_{1-3}$alkoxy or an aryloxy group, a methanesulphonyloxy, tosyloxy or benzenesulphonyloxy group, an imidazolyl radical or the residue of an N-acylhydroxylamine derivative, for example where Z is succinimidoxy, phthalimidoxy or benzotriazolyloxy. Preferred examples are those compounds in which Z is the residue of an N-acylhydroxylamine for instance the N-hydroxysuccinimide esters prepared by use of 1-cyclohexyl-3-(2-morpholinoethyl)-carbodiimide metho-p-toluenesulphonate or 1,3-dicyclohexyl-carbodiimide, or via a mixed anhydride such as that obtained by using isobutyl chloroformate. When Z is an imidazolyl radical it can be prepared by use of carbonyl di-imidazole and when Z is $R^7CO.O$, where $R^7$ is $C_{1-3}$alkyl especially ethyl and isobutyl, it can be prepared by use of 1-ethoxycarbonyl-2-ethoxy-1,2-dihydroquinoline and isobutyl chloroformate, respectively.

Compounds of formula (II) are prepared by reacting the corresponding free acid in which Z in the above formula (II) is OH, with the appropriate activating molecule, in an inert solvent such as for example dimethylformamide and preferably at a temperature of from $-20°$ C. to $75°$ C. The free acids (Z is OH) are prepared according to the following methods:

First the appropriate 4-desacetyl indole-dihydroindole is prepared by the procedure of, for example, Hargrove (U.S. Pat. No. 3,392,173).

The 4-desacetyl compound is then acylated with a carboxylic acid anhydride of the formula

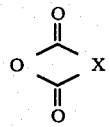

in which X has the values given above. Alternatively, as acylating group of the formula $Z^1COXCOZ^2$ in which $Z^1$ is an activating group and $Z^2$ is a carboxy protecting group, can be used, and the carboxy protecting group removed to yield the compound of formula (II) in which Z is OH. Such compounds are then converted to the activated compound by reaction with the appropriate activating molecule.

When an indole-dihydroindole is to be reacted with succinic anhydride or the like to prepare a compound of formula (II) wherein $R^1$ is COOH, the C-3 ester group as well as the C-4 ester group must be hydrolyzed initially to yield, for example from VLB, a 4-desacetyl vinblastinoic acid—see U.S. Pat. No. 4,012,390. Next, the C-3 carboxyl group must be protected with a carboxy protecting group as defined above. This C-3 carboxy protected derivative having a free hydroxyl at C-4 is then reacted as above with an anhydride. The resulting compound can then be manipulated chemically to yield compounds according to (II) in which Z is an activating moiety provided reaction conditions are neutral or basic, thus avoiding removal of the C-3 carboxy protecting group. After the desired terminal group, Z, is in place, the carboxy protecting group at C-3 can be removed to yield compounds according to (II) in which $R^1$ is COOH.

When X in the compound to be prepared is hydroxy, dihydroxy or tetrahydroxy $C_{1-4}$alkylene; i.e., a linking group derived from malic, tartaric acid or saccharic acid, it is necessary in preparing the compounds to protect the hydroxy or hydroxyls with a protecting group such as a pyranyl group. A trialkylsilyl group such as a trimethylsilyl group can also be used. In the instance of a vicinal dihydroxy compound such as tartaric acid, an acetal; i.e., an isopropylidene or cyclohyeoxylidene derivative, can be used.

When X is a direct bond (the linking group is formed from oxalic acid), oxalylchloride cannot be used since the hemioxalate may cyclize with the 3-hydroxyl. However, an oxalate half ester or an oxalic acid derivative of the formula $Cl-CO-CO-Z^2$ can be used and the ester hydrolyzed or the carboxy protecting group removed during the simultaneous conversion to an activated moiety, $R-CO-CO-Z^1$.

Reaction of immunoglobulin or immunoglobulin fragment with compound of formula (II) is preferably carried out in an aqueous medium and at a temperature of from $5°$ C. to $25°$ C., for example at room temperature, and at a pH of 7.5 to 9.5, preferably 8.0 to 9.0. The process results in the attachment by covalent linkage of one or more vinca residues at the free amino groups of the immunoglobulin molecule, for example, amino groups derived from lysine residues. The number of residues attached will depend on the concentration of the reactants and the duration of the reaction but the average number is usually for example from 1 or 3 to 14 or 20.

For example in carrying out the reaction, a solution of the compound of formula (II) in a suitable solvent such as dimethylformamide is slowly added dropwise to a buffered solution of immunoglobulin in for example 0.34M borate buffer at pH 8.6. The conjugate is isolated by gel filtration and stored in saturated ammonium sulphate solution being readily brought back into solution by dialysis with a buffer solution for example a phosphate buffered saline pH 7.4, or alternatively it can be stored in a refrigerator at $4°$ C. or frozen at for example $-20°$ C.

Evaluation of the conjugate can be carried out using well known techniques such as affinity chromatography. The efficacy of the conjugate can be estimated by counting the number of viable cells after treatment of a suspension of tumour cells with the conjugate, or from measurements of the uptake of tritiated uridine. Protein and drug concentrations are determined by measuring optical densities of conjugate solutions at two wavelengths, for example 270 and 280 nm, and relating the values obtained to those for the free drug and unconjugated immunoglobulin at the same two wavelengths.

The novel conjugates of the ivention are useful in the treatment of cancers and as such are preferably prepared for use in formulations suitable for injection. Thus the invention includes a pharmaceutical formulation, for example an injectable preparation, comprising a conjugate of the invention together with a pharmaceutically-acceptable carrier or diluent such as are well known in the art. It is preferably in unit dosage form each dosage containing for example from 0.01 to 2 mg of the active ingredient (in terms of the vinca drug moiety).

The novel conjugates are effective over a wide dosage range and for example for the treatment of adult humans dosages per week will normally fall within the range of 1 to 10 mg/kg (vinca drug moiety) more usually in the range of from 3 to 9 mg/kg. However it will be understood that the amount of compound actually administered will be determined by a physician in the light of the relevant circumstances, including the condition to be treated and the chosen route of administration. The invention is illustrated by the following Preparations and Examples.

PREPARATION 1

4-Succinoyl-desacetylvinblastine

Two g of 4-desacetylvinblastine were dissolved in pyridine to which solution were added 2 g of succinic anhydride. The reaction mixture was stirred at ambient temperature for 5 hours. (Temperatures in the range 0°–50° C. may be used for this reaction). The volatile constituents were removed by evaporation in vacuo and the residue taken up in $CH_2Cl_2$. The $CH_2Cl_2$ layer was washed with 5% aqueous sodium bicarbonate, and then with water. The organic layer was dried and the solvent removed therefrom in vacuo to give 4-succinoyl-desacetylvinblastine.

The above procedure was used to prepare the following 4-succinoyl-vindesine
4-succinoyl-desacetylvincristine
4-succinoyl-4'-epideoxydesacetylvinblastine A similar procedure was used to prepare 4-glutaroyl desacetylvinblastine using glutaric anhydride in place of succinic anhydride.

In any of the above acylations, any incidental acylation of the 3-OH group can be reversed by treatment with wet silica gel, according to the procedure of Hargrove, U.S. Pat. No. 3,392,173. Alternatively, the compounds can be purified from any 3-acyl derivative or other by-products of the reaction by chromatography, conveniently over silica gel with an ethyl acetate/methanol solvent mixture as the eluant.

PREPARATION 2

Activated 4-succinoyl-desacetylvinblastine

One gram of 4-succinoyl-vindesine was mixed with 380 mg of N-methylmorpholine in 20 ml of methylene dichloride, and 390 mg of isobutyl chloroformate were added. The reaction mixture was stirred at about 0° C. under a nitrogen atmosphere for about 45 minutes. 795 mg of N-hydroxysuccinimide were added and the reaction mixture heated at reflux temperature under $N_2$ with stirring for about 45 minutes. The reaction mixture was cooled and the cooled mixture washed with deionized water and then dried immediately with $Na_2SO_4$. The drying agent was separated by filtration and the filtrate evaporated to dryness in vacuo.

EXAMPLE 1

Vindesine-succinoyl-rabbit anti-mouse IgG conjugate

To a solution of 4-succinoyl-vindesine (25 mg) in dry dimethylformamide (DMF) (0.4 ml) was added with stirring 0.3 ml of an 11.4 mg/ml solution of N-hydroxysuccinimide in dry DMF, followed by 0.3 ml of a 41.7 mg/ml solution of 1-cyclohexyl-3-(2-morpholinoethyl)-carbodiimide metho-p-toluenesulphonate in dry DMF. The mixture was kept at room temperature in the dark for 48 hours giving a 25 mg/ml solution of 4-succinoyl-vindesine N-hydroxysuccinimide ester.

90 μl of the above solution was added with rapid stirring to 0.9 ml of a 10.7 mg/ml solution of rabbit anti-mouse IgG in 0.34M borate buffer pH 8.6. The mixture was stirred at room temperature for 5.5 hours and the product isolated by gel filtration on a 1×27 cm (21 ml) column of Bio-Gel P-6 equilibrated with phosphate buffered saline. The excluded peak was collected (4.9 ml) and assayed for protein and vindesine by spectroscopy at 270 and 280 nm. The conjugate so prepared contained 7.9 moles vindesine per mole of Ig.

EXAMPLE 2

Vindesine-succinoyl-mouse-monoclonal anti-osteogenic carcinoma conjugate

300 μl of a 28 mg/ml solution of 4-succinoyl-vindesine N-hydroxysuccinimide ester in dry DMF, prepared in a similar manner to that described in Example 1, was added with rapid stirring to 1.5 ml of a 19.8 mg/ml solution of mouse-monoclonal anti-osteogenic sarcoma in 0.34M borate buffer pH 8.6. The mixture was stirred at room temperature for 4 hours, then clarified by centrifugation and the product isolated by gel filtration of the supernatant on a 1.5×26.5 cm (46.8 ml) column of Bio-Gel P-6, equilibrated with phosphate buffered saline. The excluded peak was collected (5.52 ml) and assayed for vindesine and protein by spectroscopy at 270 and 280 nm. The conjugate so prepared contained 8.7 moles vindesine per mole of Ig.

EXAMPLE 3

Vindesine-succinoyl-mouse-monoconal anti-melanoma antigen conjugate

200 μl of a 20 mg/ml solution of 4-succinoyl-vindesine N-hydroxysuccinimide ester in dry DMF, prepared in a similar manner to that described in Example 1, was added with rapid stirring to 1.0 ml of a 21.2 mg/ml solution of mouse-monoclonal anti-melanoma antigen in 0.34M borate buffer pH 8.6. The mixture was stirred at room temperature for 4 hours and the product isolated by gel filtration on a 1.5×26 cm (45.9 ml) column of Bio-Gel P-6 equilibrated with phosphate buffered saline. The excluded peak was collected (12.31 ml) and assayed for vindesine and protein by spectroscopy at 270 and 280 nm. The conjugate so prepared contained 9.1 moles vindesine per mole of Ig.

EXAMPLE 4

Vindesine-succinoyl-mouse-monoclonal-anti-carcino-embryonic-antigen conjugate 1.0 ml of a 22 mg/ml solution of 4-succinoyl-vindesine N-hydroxysuccinimide ester in dry DMF, prepared in a similar manner to that described in Example 1, was added with rapid stirring to 7.0 ml of a 21.4 mg/ml solution of mouse-monoclonal anti-carcinoembryonic antigen in 0.34M borate pH 8.6. The reaction was stirred at room temperature for 4 hours, then diluted with 3.5 ml of 0.7M sodium chloride/0.05M phosphate buffer pH 7.4 and the product isolated by gel filtration on a 3.2×24.4 cm (196 ml) column of Bio-Gel P-6 equilibrated with phosphate buffered saline. The excluded peak was collected (28.24 ml) and assayed for vindesine and protein by spectroscopy at 270 and 280 nm. The conjugate so prepared contained 5.8 moles vindesine per mole of Ig.

EXAMPLE 5

Desacetylvinblastine-succinoyl-rabbit anti-mouse Ig conjugate

To a solution of 4-succinoyl-desacetylvinblastine (18 mg) in dry DMF (0.4 ml) was added with stirring 0.3 ml of a 7.97 mg/ml solution of N-hydroxysuccinimide in dry DMF, followed by 0.3 ml of a 14.4 mg/ml solution of 1,3-dicyclohexylcarbodiimide in dry DMF. The mixture was kept at room temperature in the dark for 19 hours giving an 18 mg/ml solution of 4-succinoyl-desacetylvinblastine N-hydroxysuccinimide ester.

200 µl of the above solution was added with rapid stirring to 1.8 ml of an 8.02 mg/ml solution of rabbit anti-mouse Ig in 0.34M borate buffer pH 8.6. The mixture was stirred at room temperature for 3.5 hours, then clarified by centrifugation and the product isolated from the supernatant by gel filtration on a 1.5×25 cm (44 ml) column of Bio-Gel P-6 equilibrated with phosphate buffered saline. The excluded peak was collected (6.47 ml) and assayed for desacetylvinblastine and protein by spectroscopy at 270 and 280 nm. The conjugate so prepared contained 9.0 moles desacetylvinblastine per mole of Ig.

EXAMPLE 6

Desacetylvincristine-succinoyl-mouse-monoclonal anti-melanoma antigen conjugate

To a solution of 4-succinoyl-desacetylvincristine (10 mg) in dry DMF (0.1 ml) was added with stirring 0.2 ml of a 6.5 mg/ml solution of N-hydroxysuccinimide in dry DMF, followed by 0.2 ml of a 24.0 mg/ml solution of 1-cyclohexyl-3-(2-morpholinoethyl)-carbodiimide metho-p-toluenesulphonate in dry DMF. The mixture was kept at room temperature in the dark for 65 hours giving a 20 mg/ml solution of 4-succinoyl-desacetylvincristine N-hydroxysuccinimide ester.

200 µl of the above solution was added with rapid stirring to 1.0 ml of a 22.7 mg/ml solution of mouse-monoclonal anti-melanoma antigen in 0.34M borate buffer pH 8.6. The mixture was stirred at room temperature for 4 hours and the product isolated by gel filtration on a 3.2×24.5 cm (197 ml) column of Bio-Gel P-6 equilibrated with phosphate buffered saline. The excluded peak was collected (14.16 ml) and assayed for protein and desacetylvincristine by spectroscopy at 270 and 280 nm. The conjugate so prepared contained 14.3 moles of desacetylvincristine per mole of Ig.

EXAMPLE 7

Desacetylvinblastine-succinoyl-mouse monoclonal anti-lung adenocarcinoma conjugate 350 µl of 14.7 mg/ml solution of 4-succinoyl-desacetylvinblastine N-hydroxysuccinimide ester, in DMF was added with rapid stirring to 2.0 ml of a 20.0 mg/ml solution of mouse monoclonal anti-lung small cell carcinoma antibody in 0.34M borate buffer pH 8.6. After stirring at room temperature for 4 hours the reaction mixture was adjusted to pH 7.4 using 1N HCl and clarified by centrifugation. The product was isolated by gel filtration on a 2.0×22.0 cm (67.0 ml) column of Bio-Gel ® P-6 equilibrated with phosphate buffered saline. The excluded peak was collected (9.7 ml) and assayed for desacetylvinblastine and protein by spectrometry at 270 and 280 nm. The conjugate so prepared contained 7.5 moles desacetylvinblastine per mole of Ig.

In a similar manner were prepared using the appropriate isolated N-hydroxysuccinimide esters:
vindesine-succinoyl-mouse monoclonal anti-carcinoembryonic antigen conjugate,
vindesine-succinoyl-mouse monoclonal anti-lung adenocarcinoma conjugate,
desacetylvinblastine-glutaroyl-mouse monoclonal anti-carcinoembryonic antigen conjugate,
4′-epideoxy desacetylvinblastine-succinoyl-mouse monoclonal anti-carcinoembryonic antigen conjugate.

EXAMPLE 8

A preparation of cells growing in culture was dispensed into microtitre tubes at a level of $10^5$ cells per tube. After concentrating the cells by centrifugation, 0.2 ml aliquots of various concentrations of conjugate preparations were added. The cells were resuspended, incubated at 37° C. for 30 minutes, then centrifuged and the supernatant removed. The cells were then suspended in tissue culture medium and dispensed into microtitre culture trays at a level of $10^4$ cells per well. After six days in culture the number of cells present in each well was determined and compared with a cell preparation treated with phosphate buffered saline alone.

In one experiment, human melanoma cells were treated with either vindesine-succinoyl-mouse-monoclonal anti-melanoma antigen conjugate (Example 3) or desacetylvincristine-succinoyl-mouse-monoclonal anti-melanoma antigen conjugate (Example 6) and the effects on cell growth determined, with the following results:

| Conjugated drug | Conjugated drug concentration, µg/ml | Cell growth as percentage of phosphate buffered saline treated control cells |
| --- | --- | --- |
| Vindesine | 50 | 16.0 |
|  | 5.0 | 61.8 |
|  | 0.5 | 84.2 |
| Desacetylvincristine | 50 | 21.5 |
|  | 5.0 | 74.5 |
|  | 0.5 | 100.0 |

In another experiment, human colo-rectal carcinoma cells were treated with vindesine-succinoyl-mouse-monoclonal anti-carcino-embryonic antigen conjugate (Example 4), with the following results:

| Conjugated drug concentration, µg/ml | Cell growth as % of phosphate buffered saline treated control cells |
| --- | --- |
| 120 | 3.2 |
| 60 | 39.9 |
| 30 | 89.9 |
| 15 | 104.8 |

EXAMPLE 9

In order to test the in vivo efficacy of the conjugates as anti-tumour agents, groups of athymic mice were implanted sub-cutaneously with cell suspensions of a human colo-rectal carcinoma and subsequently treated with intra-peritoneal injections twice weekly for five weeks. Mice were injected with either phosphate-buffered saline, mouse monoclonal antibody anti-carcinoembryonic antigen) or a vindesine conjugate of this antibody prepared as described in Example 4. The dose of antibody injected each time per mouse was between 3.3 and 3.7 mg. The dose of vindesine in the conjugate injected each time per mouse was between 119 and 128 µg.

61 Days after tumour implantation, the groups receiving PBS or antibody alone were killed, and the tumours excised and weighed. Mice receiving vindesine-antibody conjugates were killed 90 days after tumour implantation. The mean tumour weights are shown below:

| Treatment Group | No. of mice | Mean Tumour Weight (mg) ± S.D. |
|---|---|---|
| PBS | 11 | 1793 ± 1609 |
| Antibody alone | 10 | 527 ± 477 |
| Vindesine-antibody conjugate | 8 | 22 ± 19 |

We claim:

1. A cytotoxic conjugate represented by the formula $(V-COXCO-)_n Ig$ wherein V is a vinca moiety of the formula

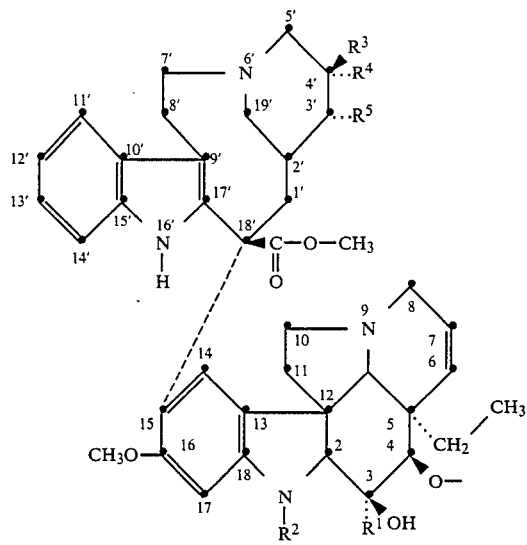

and n is 1-20 and in which Ig represents an immunoglobulin with cellular-associated antigen recognizing properties and X is $C_{1-4}$ straight chain alkylene, $C_{2-8}$ branched alkylene, $C_{2-4}$ alkenylene, $C_{3-4}$ alkynylene, $C_{3-6}$ cycloalkylene, phenylene, hydroxy-substituted $C_{1-4}$ alkylene or a direct bond; and in which $R^1$ is $COOCH_3$; $R^2$ is H, $CH_3$ or CHO; and when $R^4$ and $R^5$ are taken singly, $R^5$ is H, and one of $R^3$ and $R^4$ is ethyl and the other is H or OH: and when $R^4$ and $R^5$ are taken together with the carbons to which they are attached, they form an oxirane ring, and $R^3$ is ethyl.

2. A conjugate according to claim 1 in which the immunoglobulin is derived from an antibody to human or animal tumour associated antigens.

3. A conjugate according to claim 2 which is derived from a monoclonal antibody.

4. A conjugate according to claim 1 in which $R^1$ is COOMe, $R^2$ is methyl or formyl, $R^3$ is hydroxy, $R^4$ is ethyl, $R^5$ is hydrogen, X is $C_{1-4}$ alkylene and Ig is a monoclonal antibody to a human or animal tumor associated antigen.

5. A conjugate according to claim 4 which comprises 3 to 14 vinca residues.

6. A conjugate according to claim 1 wherein the vinca moiety is derived from 4-desacetylvinblastine.

7. A conjugate according to claim 1 wherein the vinca moiety is derived from vindesine.

8. A conjugate according to claim 1 wherein the vinca moiety is derived from 4-desacetylvincristine.

9. A conjugate according to claim 1 wherein the vinca moiety is derived from 4'-epideoxy-4-desacetyl-vinblastine.

10. A conjugate according to claim 6 wherein X is $-CH_2CH_2-$ or $-CH_2CH_2CH_2-$.

11. A conjugate according to claim 7 wherein X is $-CH_2CH_2-$ or $-CH_2CH_2CH_2-$.

12. A conjugate according to claim 8 wherein X is $-CH_2CH_2-$ or $-CH_2CH_2CH_2-$.

13. A conjugate according to claim 9 wherein X is $-CH_2CH_2-$ or $-CH_2CH_2CH_2-$.

14. A conjugate according to claim 10 wherein the immunoglobulin is adapted for recognition of human or animal colorectal carcinoma cells.

15. A conjugate according to claim 10 wherein the immunoglobulin is adapted for recognition of human or animal osteosarcoma cells.

16. A conjugate according to claim 10 wherein the immunoglobulin is adapted for recognition of human or animal carcinoembryonic cells.

17. A conjugate according to claim 10 wherein the immunoglobulin is adapted for recognition of human or animal lung adenocarcinoma cells.

* * * * *